United States Patent [19]

Shefer et al.

[11] Patent Number: 6,148,061

[45] Date of Patent: Nov. 14, 2000

[54] MINIATURE X-RAY UNIT

[75] Inventors: Ruth Shefer, Newton; Robert E. Klinkowstein, Winchester; Barbara J. Hughey, Lexington, all of Mass.

[73] Assignee: Newton Scientific, Inc., Cambridge, Mass.

[21] Appl. No.: 09/067,874

[22] Filed: Apr. 28, 1998

Related U.S. Application Data

[60] Provisional application No. 60/044,368, Apr. 28, 1997.

[51] Int. Cl.[7] .................................................. H01J 35/00
[52] U.S. Cl. ............................................. 378/121; 378/122
[58] Field of Search ...................................... 378/121, 122

[56] References Cited

U.S. PATENT DOCUMENTS

| Re. 34,421 | 10/1993 | Parker et al. . | |
|---|---|---|---|
| 3,714,486 | 1/1973 | McCrary . | |
| 4,104,531 | 8/1978 | Weiss . | |
| 4,104,532 | 8/1978 | Weiss . | |
| 4,563,769 | 1/1986 | Madsen . | |
| 5,090,043 | 2/1992 | Parker et al. ........................... | 378/121 |
| 5,153,900 | 10/1992 | Nomikos et al. . | |
| 5,199,939 | 4/1993 | Dake et al. . | |
| 5,428,658 | 6/1995 | Oettinger et al. . | |
| 5,503,613 | 4/1996 | Weinberger . | |
| 5,729,583 | 3/1998 | Tang et al. . | |

FOREIGN PATENT DOCUMENTS

| PCT/US96/ | | |
|---|---|---|
| 13629 | 8/1996 | WIPO . |
| WO 97/07740 | 3/1997 | WIPO . |
| PCT/SE98/ | | |
| 00348 | 2/1998 | WIPO . |

OTHER PUBLICATIONS

Field–Emitter Arrays for Microwave Power Tubes by Carl O. Bozler et al. of Lincoln Laboratory; Massachusetts Institute of Technology of Cambridge, MA.

Photoelectron Sources: Selection and Analysis; Nuclear Instruments and Methods in Physics Research A272 (1988) 264–267; North–Holland, Amsterdam by Peter E. Oettinger, Ruth E. Shefer, Dan L. Birx and Michael C. Green.

Basic Science Reports; Inhibition of Neointimal Proliferation With Low–Dose Irradiation From A β–Particle–Emitting Stent by John R. Laird et al.; 1996 American Heart Association, Inc.

Med. Phys. 23 (10), Oct. 1996; 1996 Am. Assoc. Phys. Med.; Dosimetry of a radioactive coronary balloon dilitation catheter for treatment of neointimal hyperplasia by H.I. Amois et al.

(List continued on next page.)

*Primary Examiner*—David P. Porta
*Assistant Examiner*—Pamela R. Hobden
*Attorney, Agent, or Firm*—Samuels, Gauthier & Stevens, LLP

[57] ABSTRACT

A miniature x-ray unit includes a first electrical node, a second electrical node and an insulating material. The first and second nodes are separated by a vacuum gap. The first node includes a base portion and a projecting portion, wherein the projecting portion and the second node are surrounded by an x-ray transmissive window through which x-rays exit the unit. The insulating material coaxially surrounds the base portion of the first node such that the insulating material is recessed from the vacuum gap, and the insulator does not extend into the vacuum gap. Recessing the insulating material from the vacuum gap decreases the likelihood that the insulator will electrically break down due to the accumulation of electrical charge, and/or the accumulation of other materials on the surface of the insulator. In a preferred embodiment, the first node is an anode and the second node is a cathode. Alternatively, the first node may be the cathode and the second node may be the anode. The cathode is preferably a cold gated field emitter array (FEA) which provides a electron current having a magnitude that is sufficient to satisfy the time constraints on x-ray dose delivery.

28 Claims, 6 Drawing Sheets

OTHER PUBLICATIONS

IEEE Transactions on Electron Devices, vol. 38, No. 10, Oct. 1991; A Study of Field Emission Microtriodes by C.E. Holland et al.

Med. Phys. 23 (1), Jan. 1996; 1996 Am. Assoc. Phys. Med.; A new miniature x-ray device for interstitial radiosurgery: Dosimetry by J. Beatty et al.

Med. Phys. 23 (1), Jan. 1996; 1996 Am. Assoc. Phys. Med.; A new miniature x-ray source for interstitial radiosurgery; Device description by M. Dinsmore et al.

Temporal Evolution of Beam Emittance and Cathode Plasma Uniformity From a Field Emission Diode by F. Hartemann et al.; from Proceedings of the IEEE Particle Accelerator Conference, Washington, D.C., Mar. 16–19, 1987.

MINIATURE X-RAY UNIT

PRIORITY INFORMATION

This application claims priority from U.S. Provisional application designated Ser. No. 60/044,368, filed Apr. 28, 1997.

BACKGROUND OF THE INVENTION

The invention relates to an insertable, miniature x-ray source for intravascular irradiation following percutaneous transluminal coronary angioplasty (PTCA) for the treatment of coronary artery disease.

Coronary artery disease is currently the leading cause of death in the United States. In coronary artery disease, fatty deposits called plaque accumulate on the walls of the coronary arteries. These deposits cause stenosis (narrowing of the lumen) and, in advanced cases, can cause complete occlusion of the artery leading to myocardial infarction and possibly death. The most widely used and successful treatment for coronary artery disease is balloon angioplasty, a procedure in which a deflated balloon is passed through a catheter to the site of an arterial stenosis and inflated to compress the plaque deposits and restore the patency of the lumen. While balloon angioplasty has a very high rate of success in terms of opening the lumen, 40–60 % of patients suffer restenosis at the site of the angioplasty within 6 months of the procedure. The mechanism of restenosis is thought to be the abnormal proliferation of injured smooth muscle cells at the treatment site, resulting in neointima formation and renarrowing of the lumen.

Animal and early clinical studies have shown that irradiation of the arterial wall to a dose of 15–20 Guy following PTCA has the effect of preventing or significantly delaying restenosis. Irradiations to date have been performed using external x-ray beams or radioactive sources. External beams have the disadvantage that radiation dose is delivered to a large volume of healthy tissue concurrent with dose delivery to the treatment site. Radioactive sources, on the other hand, can be guided to the treatment site via the same arterial catheter used to position the angioplasty balloon, making possible localized dose delivery. Vascular brachytherapy using the gamma emitter $^{192}$Ir or the $\beta^-$-emitters 32P, $^{90}$Sr, $^{90}$Y, $^{166}$Ho, or $^{188}$Re is being investigated by several research groups. These radioisotopes have half-lives of fourteen days to twenty-seven years and radiation penetration depths in tissue of approximately three millimeters to several centimeters.

The use of radioactive sources for vascular brachytherapy suffers several significant drawbacks. First, because therapy must be delivered within a short time window, high radioisotope activities in the range 50–200 mCi are required. Thus, extreme care must be taken to insure that insertion and withdrawal of the source are sufficiently rapid that dose delivered to other parts of the artery are within acceptable limits, and that the entire radioactive source is withdrawn intact from the patient. Handling of the source by physicians and other hospital personnel must be minimized and strict controls must be instituted to insure safe storage when not in use. In the case of the high energy gamma emitter $^{192}$Ir for example, the patient must be isolated and the source inserted through an automated catheter afterloader to prevent unacceptable dose to other personnel in the catheter laboratory. This procedure is clearly not compatible with usual practice during coronary catheterization in which the interventional cardiologist and other staff work in close proximity to the patient. When beta-emitters are used, isolation of the patient is not required because of the relatively short range of the $\beta$ radiation, but storage, handling, and periodic replacement of sources is still required.

In addition to the practical drawbacks described above, radioactive sources are limited in their dosimetric characteristics. Each radioisotope has a dose vs. depth profile which is fixed by the types and energies of its radioactive emissions. Thus, the dose profile cannot be adjusted to meet the requirements of a particular treatment scenario.

International application PCT/US96/13629 published Mar. 6, 1997 discloses an electronic x-ray catheter that is small and flexible enough to access an intended site within a vascular system of the body, such as the coronary arteries of the cardiovascular system. The catheter includes a flexible catheter shaft having a distal end and an electronic x-ray unit coupled to the distal end. The electronic x-ray unit comprises an anode, a cathode and an insulator that define a vacuum. A problem with this x-ray unit is that the insulating material extends into an x-ray aperture through which x-rays escape from the unit. The presence of the insulator constrains the dose depth profile that can be produced by the unit. In addition, extending the insulator into the region radially surrounding the gap between anode and the cathode can lead to an eventual breakdown of the insulator. This is because the insulator will be exposed to charged particles and neutral particles produced in the gap between the anode and the cathode. Furthermore, the geometry disclosed in this published application establishes electric field lines which can lead to insulator breakdown due to charged particles from the anode following the field lines to the insulator.

Therefore, there is a need for an improved miniature x-ray unit and techniques for irradiating an arterial wall.

SUMMARY OF THE INVENTION

An object of the present invention is to provide an electronic x-ray unit.

A further object is to provide an electronic x-ray unit for vascular brachytherapy.

Briefly, according to the present invention, a miniature x-ray unit comprises a first electrical node, a second electrical node and an insulating material. The first and second nodes are axially separated by a vacuum gap, and the first node includes a base portion and a projecting portion, wherein the projecting portion and the second node are radially adjacent to an x-ray transmissive window through which x-rays exit the unit, and the insulating material coaxially surrounds the base portion of the first node and is recessed from the vacuum gap.

Significantly, recessing the insulating material from the vacuum gap decreases the likelihood that the insulator will electrically break down due to the accumulation of electrical charge, and/or the accumulation of other materials on the surface of the insulator.

In a preferred embodiment, the first node is an anode and the second node is a cathode. Alternatively, the first node may be the cathode and the second node may be the anode.

The cathode is preferably a cold gated field emitter array (FEA) which provides an electron current having a magnitude that is sufficient to satisfy the time constraints on x-ray dose delivery. The current may be continuous or pulsed. A continuous current of at least 10–100 $\mu$A is preferred, however lower currents (down to about 1 nanoampere) are also useful and may be preferable under certain treatment conditions. The cathode is located within a miniature vacuum (i.e., evacuated) chamber in close proximity to the anode, which is maintained at a voltage of up to about 50 kV. Electrons impinge on the anode in a geometry which allows the emitted x-ray flux to escape from the anode uniformly in azimuthal angle. A transmissive x-ray window (e.g., cylindrically shaped) surrounds the vacuum gap and allows the x-rays to irradiate the inner wall of a nominally cylindrical artery.

The x-ray window material is selected to provide maximum transmission of the desired portion of the x-ray spectrum, depending on the optimum radiation penetration depth profile for a particular treatment scenario.

These and other objects, features and advantages of the present invention will become apparent in light of the following detailed description of preferred embodiments thereof, as illustrated in the accompanying drawings.

DETAILED DESCRIPTION OF THE ILLUSTRATED EMBODIMENT

Figure 1:
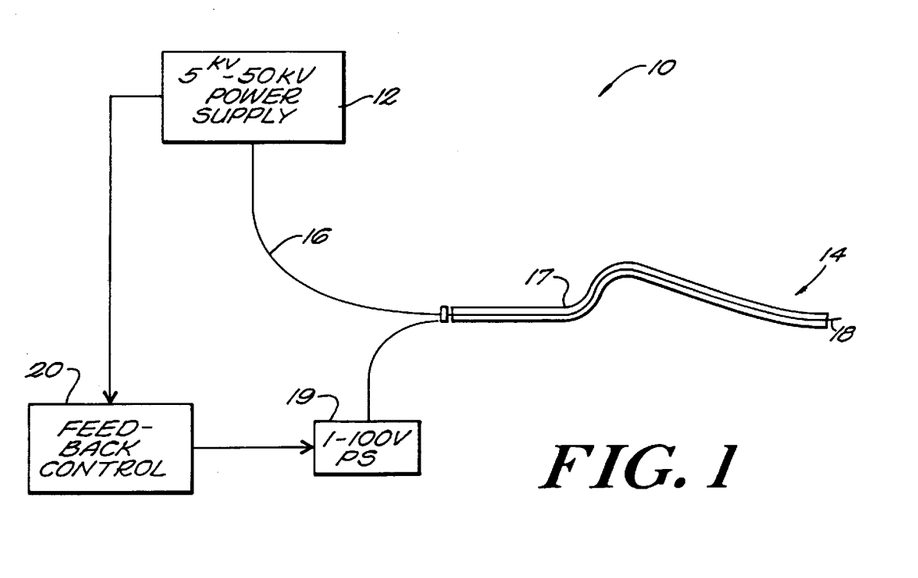
FIG. 1 is a functional illustration of a miniature electronic x-ray unit and ancillary equipment.

FIG. 1 is a functional illustration of a miniature x-ray system 10. The system includes a power supply 12 that is connected to a miniature x-ray unit 14 via a flexible cable 16. The power supply 12 produces voltages in the range 5 kV to 50 kV and supplies currents of at least about 10 $\mu$a to the x-ray unit 14. The power supply 12 is preferably a cascade multiplier-type power supply that provides high voltage stability and low stored energy. Alternately, other types of high voltage power supplies may also be used.

The invention shall be discussed in the context of intravascular irradiation. However, one of ordinary skill will recognize that the inventive x-ray unit may be used in various fields including non-medical applications such as non-destructive evaluation of metals or other structural material.

The electronic x-ray unit 14 is sized for insertion through a standard coronary guide catheter 17 so that the unit 14 slides easily through the catheter 17 and protrudes at least 0.5 cm and up to about 10 cm from an end portion 18 of the catheter. A gate voltage in the range 1–100 volts may also be supplied to the x-ray unit 14 from a second power supply 19 when a gated field emitter array (FEA) cathode is used in the x-ray unit 14. The details of the cathode will be discussed below. A feedback controller 20 controls the second power supply 19 to set the correct current level.

Figure 2:
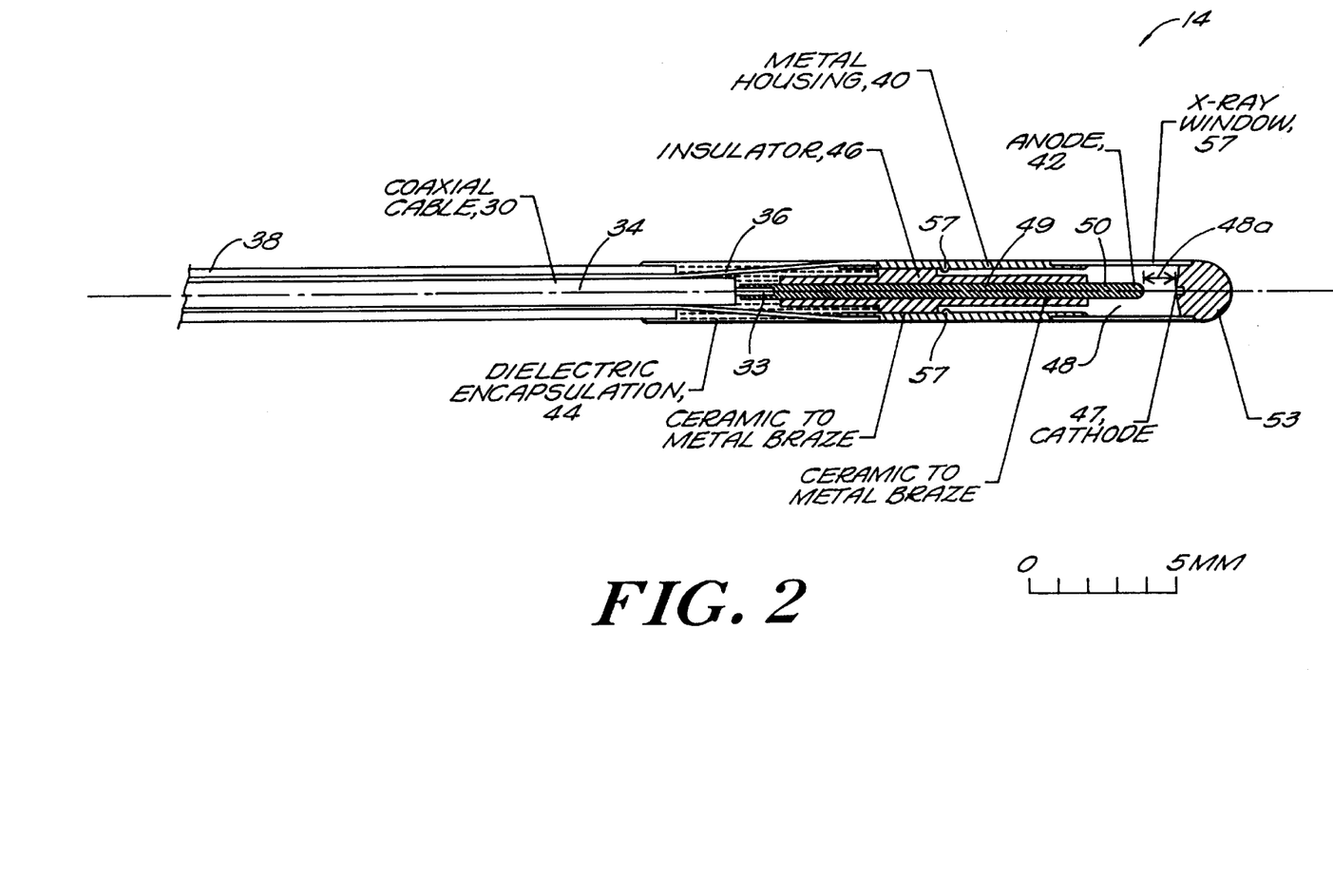
FIG. 2 is a cross-sectional diagram of the miniature electronic x-ray unit.

FIG. 2 illustrates a cross sectional view of the x-ray unit 14 which passes through the catheter 17 (FIG. 1). The x-ray unit is preferably about 0.5–2.0 cm in length so that it can be successfully fed through arterial systems which have regions of high tortuosity. In addition, the unit may be disposed of after each use, or sterilized and reused one or more times.

The x-ray unit 14 includes a flexible coaxial cable 30 comprising a inner (e.g., a center) conductor 33, plastic insulation 34, outer conductor 36 and an outer sheath 38. The sheath 38 is preferably Teflon for good biocompatibility, but other biocompatible materials can also be used. The cable insulation must have good voltage holding capabilities to withstand the application of DC voltages of at least 30 kV, and preferably up to about 50 kV. Teflon and polyethylene are examples of such plastics. The cable 30 must be flexible enough to withstand bending with a radius of curvature of at least several millimeters. An example of a suitable cable is RG178B/U which is available from many commercial suppliers in the United States.

The outer conductor 36 tapers slowly outward in radius to connect smoothly with a grounded metal housing 40 such as stainless steel, aluminum or titanium (or any other metallic material with good vacuum properties), which is coated with a biocompatible material. An important characteristic of the x-ray unit 14 is that its exterior is maintained at ground potential.

The inner conductor 33 is electrically and mechanically connected to an anode 42 in a geometry which avoids sharp edges. The space between the outer and inner conductors is filled with a dielectric material 44 which is preferably flexible and has a dielectric constant substantially equal to the plastic cable insulation. Examples of such materials are Teflon, epoxy and silicon rubber encapsulating compound. The filling is done to eliminate voids, bubbles or foreign materials. The dielectric material 44 also seals to an insulator 46 that forms one boundary of a vacuum region 48 in which the electron beam is formed between the anode 42 and a cathode 47. The vacuum region 48 includes a vacuum gap 48a which is the region between the anode and the cathode.

The insulator 46 holds-off the high voltage between the anode 42 and the grounded metal housing 40. The insulator 46 may have a tapered shape to reduce the surface electric fields along the insulator between the anode 42 and the grounded metal housing 40. If a FEA cathode is used, the insulator must contain no organic compounds. From the point of view of ease of fabrication, ceramic is a preferred insulator, although glass or mica may also be used. An example of a suitable ceramic is alumina. The insulator 46 is bonded (e.g., brazed) to the metal housing 40. Protrusions 51 in the metal housing 40 on the vacuum side close to the metal-to-ceramic interface serve to shield the electric field at the interface to reduce the probability of high voltage breakdown along the surface of the insulator 46.

The anode 42 includes a base portion 49 and a projecting portion 50, wherein the insulator 46 is recessed from the anode projecting portion 50 and coaxially surrounds only the base portion 49; not the projecting portion 50. Significantly, recessing the insulator 46 from the vacuum gap 48 decreases the likelihood that the insulator 46 will electrically breakdown due to the accumulation of electrical charge.

The anode 42 is bonded (e.g., brazed) to the insulator 46 and the bond is preferably made as close as possible to the distal end of the insulator to eliminate regions of field enhancement. Tungsten is a suitable anode material, as are other high-Z conductors such as molybdenum, gold, tantalum or depleted uranium. It is well known that use of a high-Z metal increases the production of x-rays when accelerated electrons strike the anode 42.

The cathode 47 is maintained at ground potential and the anode 42 at positive high voltage. This configuration is electrically advantageous compared to maintaining the cathode 47 at a high negative voltage relative to a grounded anode. The cathode 47 is mounted in the distal end of the metal housing 40 and the end of the housing includes a rounded nose 53 to facilitate insertion through the guide catheter and artery lumen.

Figure 3:
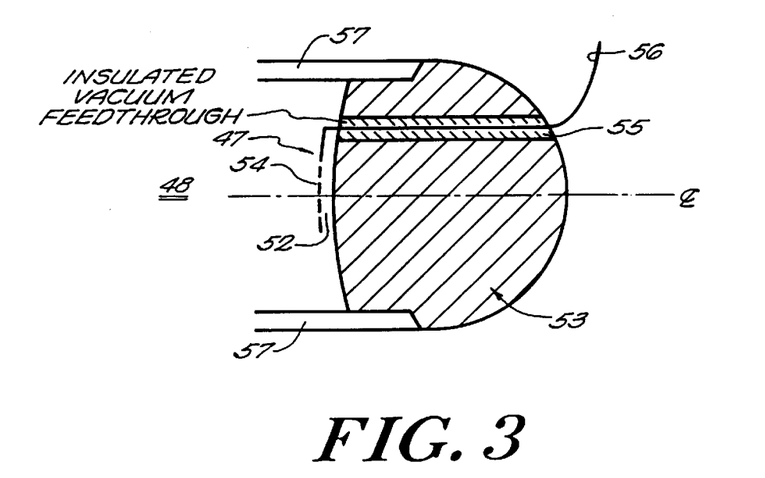
FIG. 3 is a cross-sectional illustration of the nose region of the electronic x-ray unit.

FIG. 3 is a cross-sectional illustration of the nose region of the electronic x-ray unit 14. The cathode 47 is preferably a gated field emitter array (FEA) that includes microscopic metal tips 52 (e.g., molybdenum) adjacent to a gate electrode 54 maintained at a preselected voltage. By adjusting the voltage on the gate electrode 54, a very high electric field (of order 10 MV/cm) is applied to the metal tips 52, resulting in field emission of electrons from the tips 52. Continuous current densities greater than 1 A/cm$^2$ have been produced from this type of cathode (it is contemplated that a pulsed current source may also be used). Thus, a cathode of dimensions 1×mm can produce up to 10 mA of electron current. The desired currents of 10–200 $\mu$A from a 1×1 mm emitter can be easily achieved using a gate voltage of about 1–100 volts. Referring to FIGS. 2–3, the electron beam is then accelerated to the anode 42 which is maintained at a potential of about 5–50 kV. Therefore, the total power dissipated by the unit 14 is only about 0.05–10 Watts. The FEA cathode may be of the type described by: Bozler et. al. (J. Vac Sci. Technol. B12, 1994, p. 629 and IVMC Technical Digest, pp. 118–122, Portland, Oreg., Jul. 30–Aug. 3, 1996); Spindt et. al. (IEEE Trans. Electron Devices, 38 (10), pp.2355–2363, 1991); or C. E. Holland, et. al. (IEEE Trans. Electron Devices, 38 (10), pp. 2368–2372), 1991). In the interest of brevity the details set forth in these papers shall not repeated herein, and accordingly these papers are hereby incorporated by reference.

When the cathode 47 is a gated FEA, an insulator 55 in provided in the end piece 53 to electrically isolate the cathode tips 52 from the conducting substrate in order to allow the cathode 47 to be maintained at a negative voltage of about −100 volt to −1 volt relative to ground potential. The negative voltage is fed to the tip of the x-ray head via a cable 56. In this case, the gate electrode is electrically connected to the grounded housing. Alternately, the cathode tips 52 may be electrically connected to ground and a small positive voltage of 1 to 100 v. applied to the gate electrode 54.

As an alternative to a gated FEA cathode, an explosive field emission cathode may also be used in the miniature x-ray unit for vascular brachytherapy. In this type of cathode, a short duration high voltage pulse is applied to a material with favorable surface emission characteristics, such as carbon, graphite, carbon felt and velvet. Electric fields of 100 kV/cm or higher will initiate the formation of a plasma at the cathode surface from which electrons are then accelerated. This type of cathode can deliver very high current densities (e.g., greater than about 10 kA/cm$^2$), but is limited in pulse length to the time that it takes the plasma to cross the anode-cathode gap. For an anode potential of 10 kV, the largest gap compatible with the field requirement for explosive emission is about 0.1 cm. Therefore, for typical plasma velocities of 1 cm/$\mu$sec, the pulse length is limited to 0.1 $\mu$sec or less. The peak electron current must consequently be adjusted to give the desired time-average current. Other alternative cathode types include photoemitters, thermionic emitters or thermoelectric cathodes and these cathodes among others are described in more detail in the following references: Oettinger, et. al., "*Photolectron Sources: Selection and Analysis*" (Nucl. Instrum. Meth. Phys. Res. A272 (1988) p. 264–266); Hartemann, et. al., "*Temporal Evolution of Beam Emittance and Cathode Plasma Uniformity from a Field Emission Diode*" (Proc. IEEE Particle Accelerator Conference, pp. 385–387, Mar. 16–19, 1987); Brownridge, "*A Simple Solid-State X-ray Generator*" (Abstracts of the Fourteenth International Conference on the Applications of Accelerators in Research and Industry, Eds. J. L. Duggan and I. L. Morgan, Univ. of N. Texas, Nov 6–9, 1996, paper PA64, see pg. 116). In the interest of brevity the details set forth in the above identified papers shall not repeated herein, and accordingly these papers are hereby incorporated by reference.

Referring again to FIG. 2, the anode 42 and the cathode 47 are mounted within the vacuum gap 48 surrounded by an x-ray transmissive window 57 having a high x-ray transmission coefficient at energies between 1–50 keV. Low-Z materials, such as beryllium metal, ceramics, glass, plastics and mica are good transmitters of low energy x-rays. Beryllium is a favorable x-ray window material because it has a very high transmission coefficient, it is easy to fabricate and it naturally forms a part of a continuous conducting boundary surrounding the x-ray unit head. Ceramic, glass, or mica may also be used, but would need to be coated on their inner or outer surface with a thin conducting metal layer. Plastics are generally not suitable for use with FEA cathodes because they may introduce organic contaminants into the vacuum region. The x-ray window 57 is preferably cylindrical to radially transmit x-radiation produced at all azimuth angles with equal probability. Significantly, the direct path from the anode to the x-ray window 57 does not include an insulator. That is, the insulator 46 does not extend into the vacuum gap 48.

Figure 4:
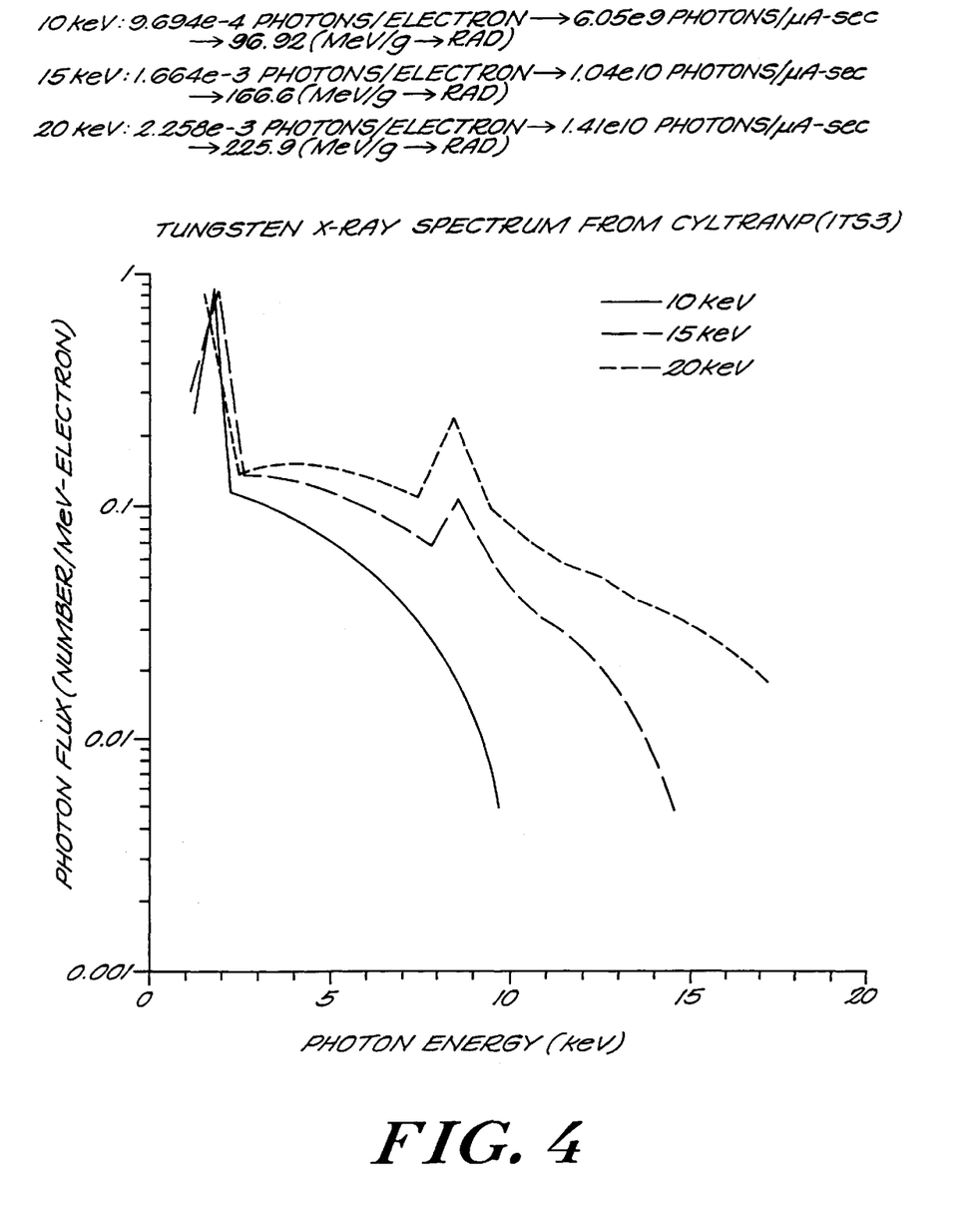
FIG. 4 is a plot of calculated x-ray spectra from 10, 15 and 20 kV electrons incident on a tungsten anode.

FIG. 4 is a plot that illustrates three calculated x-ray spectra for electrons of different energies incident on a tungsten anode. The spectra were calculated using the CyltranP (ITS3) Monte Carlo code. It is evident that increasing the electron energy both increases the emitted x-ray flux and the maximum x-ray photon energy. It is important for the anode 42 to have a smooth surface finish to reduce the probability of high voltage breakdown between the anode and other surfaces at ground potential. For this reason, a polished, spherical anode tip is preferred. One way of achieving this shape and surface finish is to bring the anode to its melting point while holding it in a vertical orientation, and allowing the tip to reform while cooling takes place.

Figure 5:
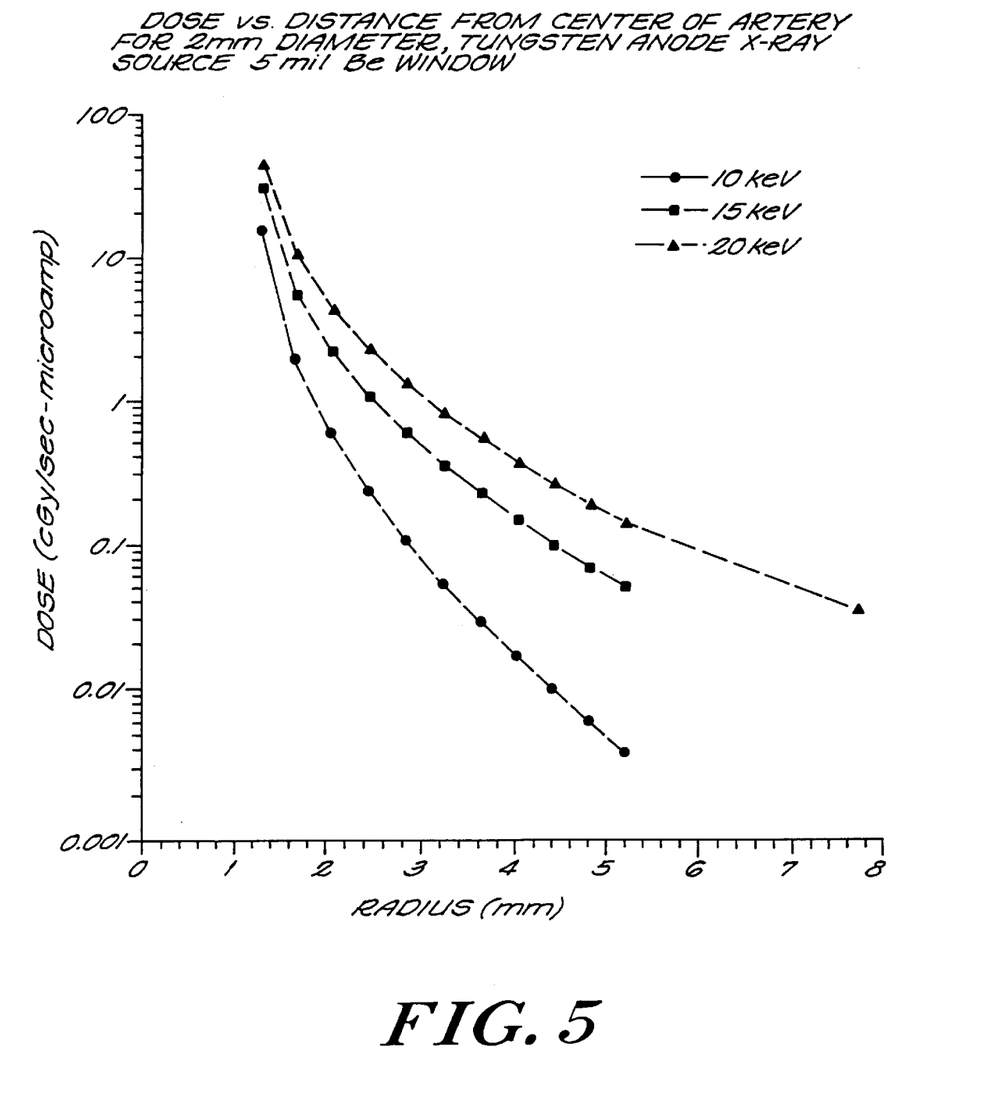
FIG. 5 is a plot of calculated dose profiles as a function of distance from the center of the artery for a 2 mm outer diameter x-ray unit with tungsten anode and beryllium window of thickness 0.005 inches.

Examples of calculated dose rates in tissue (water) outside a spherical, 2 mm diameter x-ray unit with a 0.005 inch thick beryllium x-ray window are shown in FIG. 5. The beryllium window 57 (FIG. 2) can be vacuum brazed or welded to the metal nose piece 53 at one end and to the outer housing 40 of the x-ray unit at its other end of the window 57 (FIG. 2).

Figure 6:
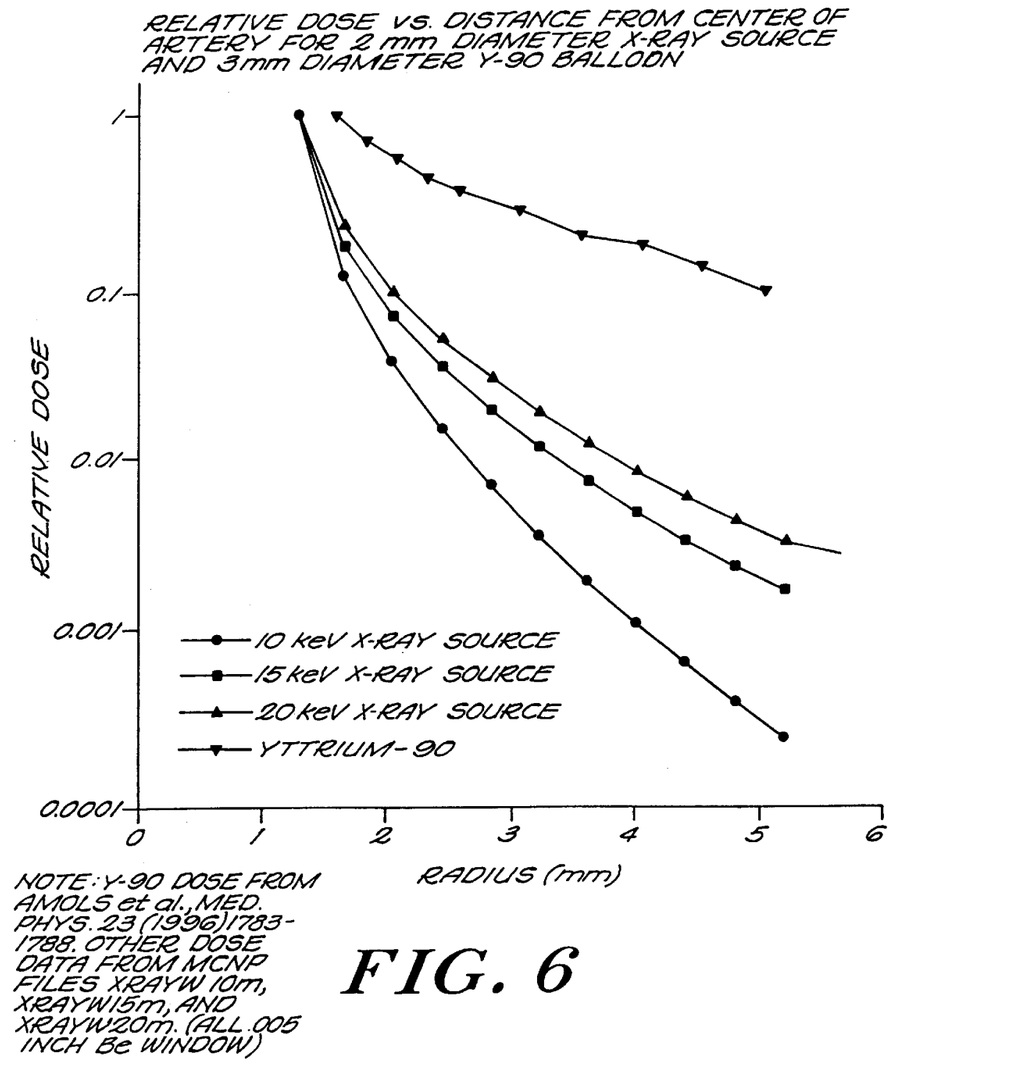
FIG. 6 is a plot of calculated relative doses as a function of the distance from the center of the artery for a 2 mm outer diameter x-ray unit with a tungsten anode and a beryllium window with a thickness 0.005 inches, and for a 3 mm diameter balloon filled with Yttrium-90 solution.

One of the prospective advantages of the miniature x-ray unit compared with radioactive sources is that it can deliver its dose preferentially to the inner wall of the artery, with little dose to tissue at depth. FIG. 6 compares the relative dose rate versus depth profiles from x-rays produced by electrons of different energies with the profile produced with an Yttrium-90 (Y-90) radioactive source using a 0.005 inch beryllium window thickness. The penetration depth of the x-rays can be controlled by adjusting the energy of the accelerated electrons, as is evident from FIG. 6. For the Y-90 source, on the other hand, the depth of radiation penetration is fixed.

Figure 7:
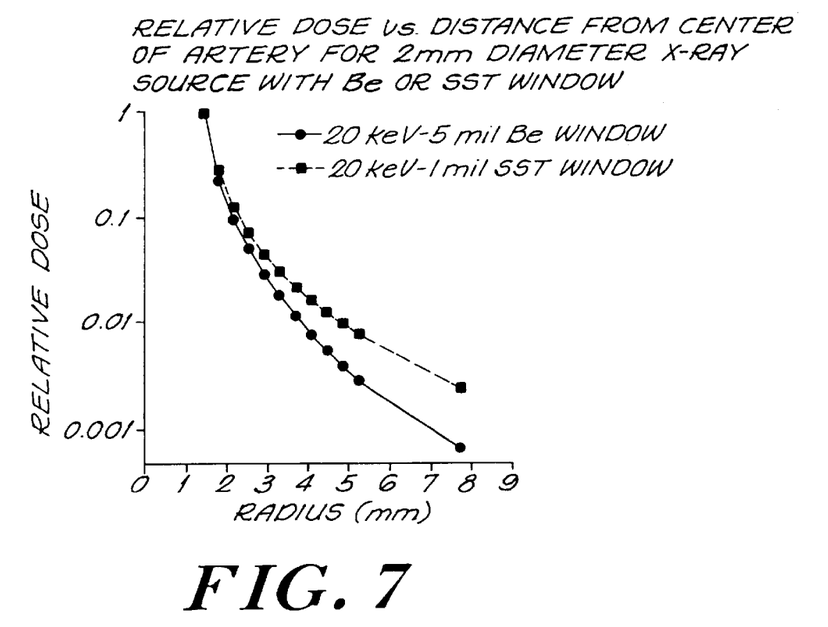
FIG. 7 illustrates a comparison of the calculated relative dose profiles as a function of the distance from the center of the artery for a 2 mm outer diameter x-ray unit with a tungsten anode and either a beryllium window with thickness 0.005 inches or a stainless steel window with thickness 0.001 inches.
Figure 8:
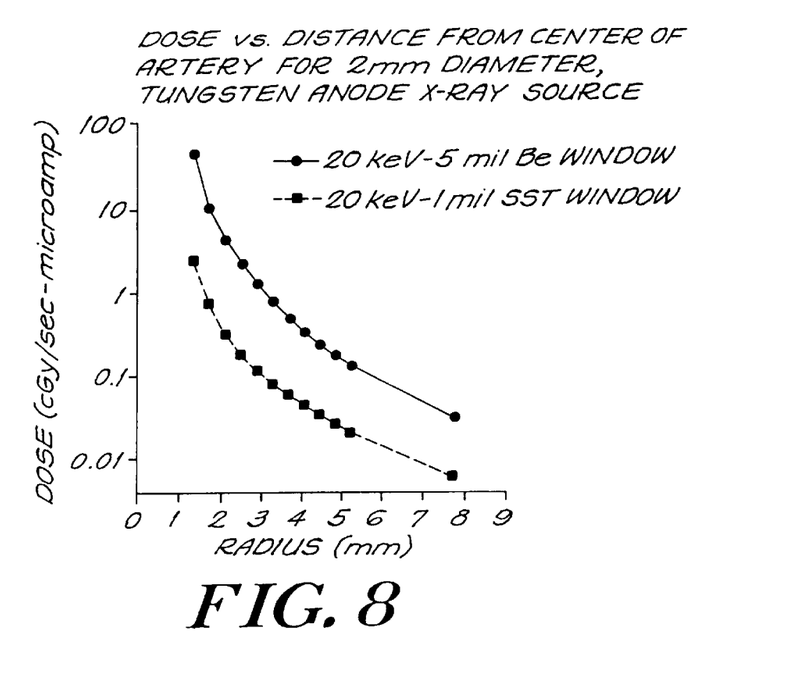
FIG. 8 illustrates the calculated absolute dose profiles as a function of the distance from the center of the artery for a 2 mm outer diameter x-ray unit with a tungsten anode and either a beryllium window with thickness 0.005 inches or a stainless steel window with thickness 0.001 inches.

When deeper penetration is required from the x-ray unit, the electron energy can be further increased over the value of 20 keV shown in FIG. 6, or a different material can be used for the x-ray window 56 (FIG. 2). The use of a window material with a higher x-ray absorption coefficient will preferentially absorb the lower energy x-rays emanating from the anode 42 (FIG. 2), resulting in a deeper penetrating x-ray spectrum. Higher-Z materials, such as stainless steel, titanium or aluminum, have higher absorption coefficients and are suitable from a fabrication and vacuum point of view for use in the x-ray unit 14. The relative dose rates versus depth in tissue from x-rays produced by 20 keV electrons and filtered by either a 0.005 inch thick beryllium window or a 0.001 inch thick stainless steel window are shown in FIG. 7. It is evident from FIG. 7 that the result of using a harder (higher energy) x-ray spectrum is a slower decrease in dose with depth in tissue. This is sometimes desirable when a large treatment depth is required. However, this slower decrease with depth comes at the expense of reduced transmission and therefore reduced dose rate, as illustrated in FIG. 8.

In all cases illustrated in FIGS. 5–8, it is evident that the dose delivered to the artery is highest near the x-ray unit 14 (FIG. 2) and decreases rapidly with depth. Therefore, it is necessary to insure that the x-ray unit is well centered in the artery to achieve uniform dose delivery around the inner wall of the artery. The x-ray unit can be centered by providing a centering balloon (not shown) or other inflatable device around the x-ray unit. Before the x-ray unit is turned on, the centering balloon would be inflated with saline, or other biologically inert solution having an x-ray absorption coefficient similar to that of blood. Alternately, a segmented balloon can be used, which does not cover the x-ray window. An example of this configuration would be a two-segment balloon, with one segment located near each end of the x-ray window. A further possible advantage of a segmented balloon is that it may be inflated with iodine contrast agent, making it visible in a fluoroscope image. The inflated balloon may thus be used as an aid in locating the x-ray unit head. A preferred method for performing therapy with this device is as follows.

While in the "off" state, the x-ray unit 14 (FIG. 2) is inserted through a guide catheter to the region of the artery requiring treatment. When the unit is positioned at the treatment site, it turned on and x-ray production commences. The unit remains enabled until the desired radiation dose (about 15–20 Gy) is delivered to the artery wall.

The dose is delivered to the portion of the artery wall approximately adjacent to the x-ray window. If dose delivery to a less extensive region is desired, prior to insertion of the unit 14, an x-ray absorbing material is placed around some portion of the x-ray window 57 (FIG. 2) to block x-rays emanating from that portion of the window. If the dose must be delivered to a portion of the artery longer than the length of the x-ray window, the unit is moved while in the "on" state along the artery lumen. This can be accomplished by feeding the x-ray unit into, or out of, the guide catheter at the insertion location. The x-ray unit is preferably moved along the length of the treatment region under computer control to insure the correct x-ray dose is delivered to each location along the artery. After treatment, the unit is turned off and removed from the guide catheter.

The x-ray unit may also be used to perform vascular brachytherapy of the coronary arteries either before or after placement of an arterial stent. In addition, the unit may be used to perform vascular brachytherapy of other arteries after balloon angioplasty or before or after stent placement. Examples of candidate arteries are the femoral or carotid arteries or other arteries of the peripheral circulation. The miniature x-ray unit may also be used to perform radiation therapy in other locations within the human body that can be reached by a flexible catheter. For example, a probe with the approximate dimensions given above may be used to reach tumors of the pancreas, liver or gall bladder via the bile ducts and pancreatic ducts and may also be used to reach the bladder, rectum, colon, kidneys, prostate gland, esophagus, stomach etc. via other body passages. For these other medical applications, the optimum geometry, current, and energy of the x-ray unit may be different from those found to be preferred for vascular brachytherapy.

The miniature x-ray unit may also be used for non-medical applications. For example, non-destructive evaluation of metals or other structural materials is often performed using an external x-ray source. In x-ray radiography, for instance, x-rays transmitted through the object are imaged to detect the presence of cracks, corrosion, wear, or other defects. The unit 14 described herein may be inserted into narrow passageways or cracks in the object and the transmitted x-rays imaged. Advantageously, x-ray flux would be concentrated near the region of interest and would not have to traverse the entire thickness of the object. Similarly, the x-ray unit 14 may be inserted into fluid or gas passages in engines or other mechanical systems for the purpose of imaging or detecting corrosion or blockages. Another use would be for the radiographic inspection of welds in pipes or other objects. For all of these non-medical applications, the diameter, length, current and energy of the source would be selected with respect to the geometry of the object under examination and may vary from the parameters of the source described in the previous sections.

Although the present invention has been shown and described with respect to several preferred embodiments thereof, various changes, omissions and additions to the form and detail thereof, may be made therein, without departing from the spirit and scope of the invention.

What is claimed is:

1. A miniature x-ray unit, comprising:
    a conductive housing;
    a first electrical node;
    a second electrical node;
    an insulating material, wherein said first and second nodes are axially separated by a vacuum gap, and said first node includes a base portion and a adjacent to an x-ray transmissive window through which x-rays exit the unit, and said insulating material coaxially surrounds said base portion of said first node and is recessed from said vacuum gap; and
    an electrical conductor having an inner conductor electrically in contact with said first node, and an outer conductor electrically in contact with said housing to maintain said housing at ground potential.

2. The unit of claim 1, wherein said first node is an anode and said second node is a cathode.

3. The unit of claim 1, wherein said first node is a cathode and said second node is an anode.

4. The unit of claim 2, wherein said cathode comprises a gated field emitter array.

5. The unit of claim 3, wherein said cathode comprises a gated field emitter array.

6. The unit of claim 2, wherein said cathode comprises a gated field emitter array comprising a plurality of metal tips.

7. The unit of claim 3, wherein said cathode comprises a gated field emitter array comprising a plurality of metal tips.

8. The unit of claim 1, wherein said first and second nodes operate as an anode and a cathode and said x-ray transmissive window comprises at least one of beryllium, titanium, aluminum, stainless steel, ceramics, glass, plastics and mica.

9. The unit of claim 1, wherein said insulating material is in face-to-face contact with said base portion.

10. The unit of claim 1, further comprising a housing having an exterior surface and an interior surface, wherein said insulating material is in face-to-face contact with a portion of said interior surface and said exterior surface is at ground potential.

11. The unit of claim 1, wherein said first and second nodes operate as an anode and a cathode and said anode comprises at least one of tantalum, tungsten, molybdenum, gold or depleted uranium.

12. The unit of claim 6, wherein said gated field emitter array comprises a plurality of metal tips comprising molybdenum.

13. The unit of claim 2, wherein said cathode comprises an explosive field emitter.

14. The unit of claim 2, wherein said cathode comprises a thermionic emitter.

15. The unit of claim 2, wherein said cathode comprises a gated field emitter array comprising a plurality of silicon tips.

16. The miniature x-ray unit of claim 1, wherein said conductive housing comprises a metallic housing.

17. The unit of claim 16, wherein said metal housing includes protrusions on an interior side of said housing to reduce the likelihood of high voltage breakdown on the surface of the insulator.

18. The unit of claim 1, further comprising means for covering at least a portion of said x-ray transmissive window with an x-ray absorbing material to alter the spatial distribution of x-rays from the unit.

19. A miniature electronic x-ray unit, comprising:
a conductive housing;
an anode;
a cathode;
means for applying an electrical potential between said anode and said cathode;
an insulating material, wherein said anode and cathode are axially separated by a vacuum gap, and said anode includes a base portion and a projecting portion, wherein said projecting portion and said cathode are radially adjacent to an x-ray transmissive window through which x-rays exit the unit, and said insulating material coaxially surrounds said base portion and is recessed from said vacuum gap; and
means for maintaining said housing at ground potential.

20. The unit of claim 19, wherein said anode is selected from a group of high-Z materials comprising tungsten, molybdenum, gold, tantalum and depleted uranium.

21. The unit of claim 19, wherein said x-ray transmissive window is selected from a group of materials comprising beryllium, ceramics, glass, titanium, aluminum, stainless steel, plastics and mica.

22. The unit of claim 20 wherein said anode comprises a spherical tip.

23. The miniature electronic x-ray unit of claim 19, wherein said conductive housing comprises a metallic housing.

24. The method of claim 23, wherein the lumen is a blood vessel.

25. The method of claim 23, wherein the blood vessel is a coronary artery.

26. A method of performing x-ray radiography, comprising the steps of:
inserting a miniature electronic x-ray unit into a narrow passageway; and
imaging regions adjacent to the miniature electronic x-ray unit.

27. A method of irradiating a lumen in the human body, comprising the steps of:
inserting a miniature x-ray unit comprising a first electrical node, a second electrical node and an insulating material through a catheter to a site to be irradiated, wherein said first and second nodes are axially separated by a vacuum gap, and said first node includes a base portion and a projecting portion, wherein said projecting portion and said second node are radially adjacent to an x-ray transmissive window through which x-rays exit the unit, and said insulating material coaxially surrounds said base portion of said first node and is recessed from said vacuum gap;
applying power to said miniature x-ray unit which emits x-rays through said x-ray transmissive window to irradiate the lumen; and
disposing of said miniature x-ray unit following irradiation of the lumen.

28. A method of irradiating a lumen in the human body, comprising the steps of:
inserting a miniature x-ray unit comprising a housing maintained at ground potential, first electrical node, a second electrical node and an insulating material through a catheter to a site to be irradiated, wherein said first and second nodes are axially separated by a vacuum gap, and said first node includes a base portion and a projecting portion, wherein said projecting portion and said second node are radially adjacent to an x-ray transmissive window through which x-rays exit the unit, and said insulating material coaxially surrounds said base portion of said first node and is recessed from said vacuum gap; and
applying power to said miniature x-ray unit which emits x-rays through said x-ray transmissive window to irradiate the lumen.

* * * * *